United States Patent

Heffington et al.

[11] Patent Number: 5,315,384
[45] Date of Patent: May 24, 1994

[54] COLOR LINE SCAN VIDEO CAMERA FOR INSPECTION SYSTEM

[75] Inventors: Jack C. Heffington, Central Point; H. Parks Squyres, Medford, both of Oreg.

[73] Assignee: Simco/Ramic Corporation, Medford, Oreg.

[21] Appl. No.: 982,148

[22] Filed: Nov. 25, 1992

Related U.S. Application Data

[63] Continuation of Ser. No. 606,758, Oct. 30, 1990, abandoned.

[51] Int. Cl.$^5$ .............................................. H04N 7/18
[52] U.S. Cl. ................................ 348/93; 356/237; 348/95; 348/340
[58] Field of Search ............ 358/106, 101, 93, 50, 358/107, 55, 41, 76, 78, 55, 53, 10, 139; 382/17, 8, 1; 356/237, 407, 418, 425, 385, 402, 411, 416, 414, 425; 250/226, 208.1; 209/509, 517, 524, 577; H04N 7/18

[56] References Cited

U.S. PATENT DOCUMENTS

| | | | |
|---|---|---|---|
| 3,980,181 | 9/1976 | Hoover et al. | 209/582 |
| 4,323,918 | 4/1982 | Bendell | 358/50 |
| 4,567,506 | 1/1986 | Shinoda et al. | 358/101 |
| 4,587,414 | 5/1986 | Bohlander | 250/226 |
| 4,680,627 | 7/1987 | Sase et al. | 358/101 |
| 4,695,878 | 9/1987 | Levine et al. | 358/41 |
| 4,738,175 | 4/1988 | Little et al. | 83/71 |
| 4,782,390 | 11/1988 | Hayashi et al. | 358/78 |
| 4,789,891 | 12/1988 | Kanayama et al. | 358/55 |
| 4,797,738 | 1/1989 | Kashi et al. | 358/101 |
| 4,916,529 | 4/1990 | Yamamoto et al. | 358/50 |
| 4,972,494 | 11/1990 | White et al. | 358/105 |
| 4,992,949 | 2/1991 | Arden | 356/237 |
| 5,010,580 | 4/1991 | Vincent et al. | 250/226 |
| 5,072,128 | 12/1991 | Hayano et al. | 250/226 |
| 5,085,325 | 2/1992 | Jones et al. | 207/580 |

FOREIGN PATENT DOCUMENTS 0377478 11/1990 European Pat. Off. .............. 5/342

OTHER PUBLICATIONS

Image Technology (Journal of the BKSTS), vol. 68, No. 11, Nov. 1986, London, GB pp. 539-546.
Patent Abstracts of Japan, vol. 12, No. 328 (E-654) (3175) Sep. 6, 1988 & JP No. 63-90985 (Canon) Apr. 21, 1988.

*Primary Examiner*—James J. Groody
*Assistant Examiner*—Michael H. Lee
*Attorney, Agent, or Firm*—Stoel Rives Boley Jones & Grey

[57] ABSTRACT

A color line scan video camera (50) for inspecting articles (18) includes a prismatic beam splitter arrangement (52) that receives a wide spectrum of visible light from a variable magnification objective lens arrangement (54) to provide improved multi-color inspection capability. The prismatic beam splitter separates the light received from the scanned articles into three preselected spectral bands of light, each of which is imaged upon a different charge-coupled device line scan sensor that generates a corresponding color component video signal. The light transmission characteristics of the lens are "color-corrected" to transmit uniformly the light received from the scanned articles.

7 Claims, 6 Drawing Sheets

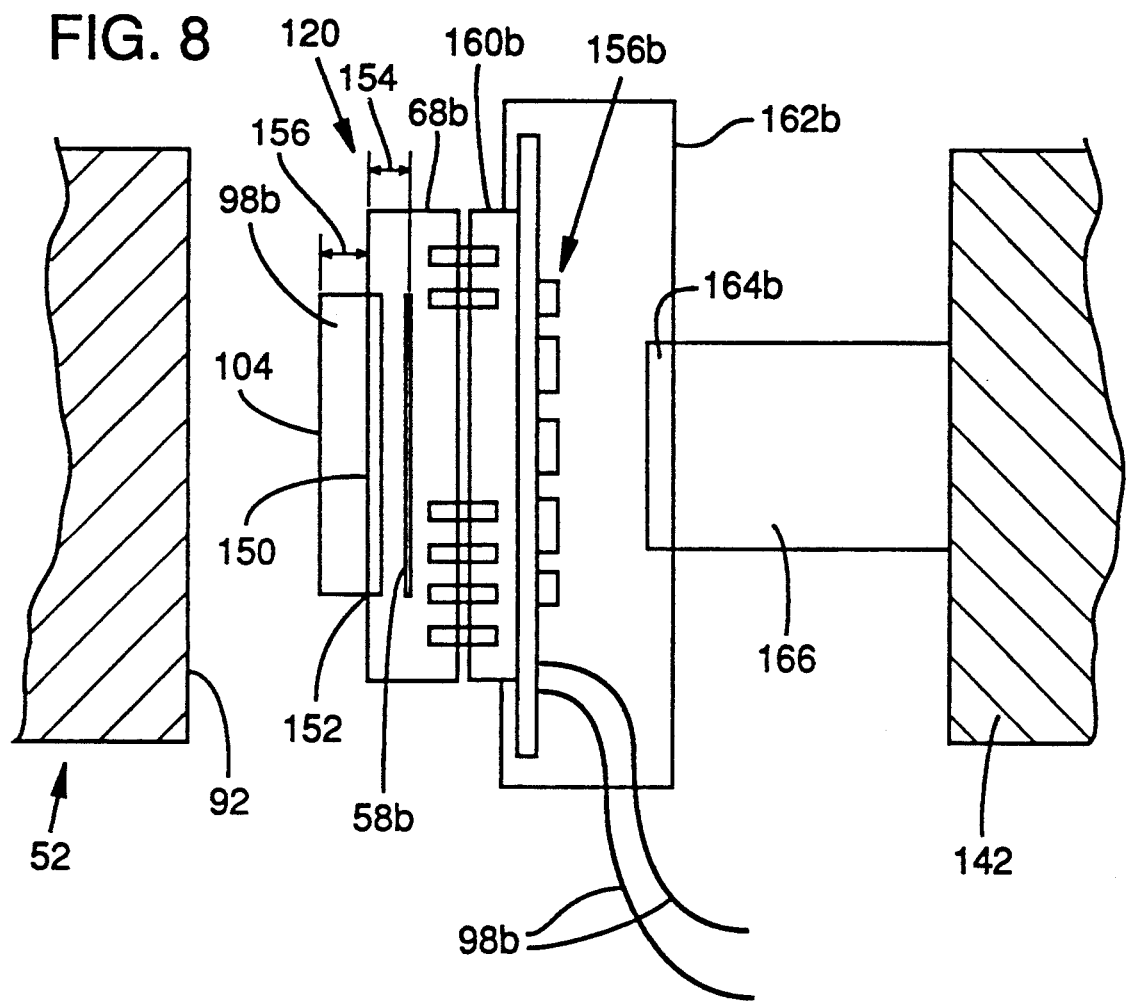

COLOR LINE SCAN VIDEO CAMERA FOR INSPECTION SYSTEM

This is a continuation of U.S. patent application Ser. No. 07/606,758 of Heffington et al. filed Oct. 30, 1990, now abandoned.

TECHNICAL FIELD

The present invention is directed to video cameras used primarily in systems for inspecting articles and, in particular, to a color line scan video camera that generates color video signals representing the color characteristics of articles moving through a line scan area.

BACKGROUND OF THE INVENTION

FIG. 1 shows an inspection system 10 having a prior art monochrome line scan video camera 12 that generates an electrical video signal representing objects aligned with a line scan area 14 having an aspect ratio of about 1024:1. Inspection system 10 inspects line segments 16 (shown as cross-hatching) of articles passing through line scan area 14. Inspection system 10 is capable of inspecting articles of various shapes and sizes such as, for example, french fry potato strips, lima beans, peas, carrots, or sliced carrots. For purposes of description, inspection system 10 is shown inspecting generally elongated articles 18, which are representative of french fry potato strips. Line segments 16 correspond to the portions of articles 18 intersected by line scan area 14.

Inspection systems used by the food product industry include a conveyor belt 22 that carries in a direction 24 large numbers (not shown) of generally elongated articles 18, such as french fried potato strips or green beans, distributed over and substantially covering conveyor belt 22. Elongated articles 18 are illuminated by a nominally white light source 26, have lengths generally aligned with direction 24, and are oriented generally perpendicular to a scanning axis 28 of line scan camera 12. Line scan camera 12 generates a video signal corresponding to the source light reflected by line segments 16 of articles 18 and the portion of conveyor belt 22 positioned in line scan area 14 during an image cycle or frame. Video signals representing substantially complete two-dimensional images of articles 18 are generated by scanning the articles during successive image frames while conveyor belt 22 carries the articles past line scan area 14. In one embodiment, inspection system 10 identifies from the video signals defects in articles 18, thereby enabling excision of the defects from the articles or the removal of articles having defects from conveyor belt 22.

Conventional line scan cameras typically employ a single 1024×1 photodetector array that provides a single gray-scale (i.e., black-and-white) representation of the scanned articles at an image frame rate of about 1000 Hz. The 1024×1 configuration of the photodetector array defines the 1024:1 aspect ratio of line scan area 14 extending across conveyor belt 22 along scanning axis 28.

A disadvantage of such cameras in defect detection systems is that defective and non-defective portions of an article may be indistinguishable in the black-and-white representation. For example, the detection of defects in green beans can be relatively difficult with a black-and-white camera because the colors corresponding to defective and non-defective regions reflect substantially equal amounts of light of different portions of the visible spectrum. Since a black-and-white representation corresponds to overall light intensity, certain defects in green beans are virtually undetectable by a line scan camera employing only one gray-scale.

Certain inspection systems employ conventional color video cameras of the raster scan area array camera type, which uses a two-dimensional (e.g., 512×512) array of photodetectors. A raster scan area array camera can work at lower frame rates, but suffers from increased complexity stemming from a need to track the articles through the two-dimensional field of view. As a consequence, such cameras are undesirably complex for high-speed inspection systems of the type used in the food product industry.

Conventional monochrome line scan cameras typically have an objective lens arrangement with a fixed magnification that allows the lens to form an image only of the complete width of the conveyor belt along the scanning axis. As a consequence, particular positions across the width of the conveyor belt are fixedly focused onto specific ones of the photodetectors in the array. Such magnification characteristics provide acceptable performance when the entire width of the conveyor belt is covered by articles to be inspected. Whenever the conveyor belt is not completely covered with articles to be inspected, however, the photodetectors upon which the uncovered portions of the conveyor belt are focused provide no inspection information.

In one type of conventional color line scan camera, each full-color pixel is generated by a triad of separate, closely positioned red-, green-, and blue-component photodetectors. The triads in such a camera are arranged in a line, with the three photodetectors of each triad having either an in-line or a delta configuration. Such cameras typically provide unpredictable edge effects, which are inaccurate representations of the color of the edges of a scanned article. The unpredictable edge effects occur when the edge of the scanned article is focused upon only some or parts of the photodetectors in a triad, thereby causing the triad to generate a false representation of the color or hue of the article. The unpredictable edge effects characteristic of this type of color line scan camera limits the resolution of such cameras in inspection systems.

To make use of all of the photodetectors under such circumstances, certain line scan camera systems may be selectively fitted with different objective lenses having different fixed magnifications. Selecting and fitting objective lenses can, however, be time consuming and require an expensive array of objective lenses to cover the range of possible fields of view.

SUMMARY OF THE INVENTION

An object of this invention is, therefore, to provide a line scan camera for use in inspection systems.

Another object of this invention is to provide such a line scan camera that is capable of generating color video signals representing color characteristics of scanned articles.

A further object of this invention is to provide such a line scan camera having an objective lens that is capable of providing variable magnification.

Yet another object of this invention is to provide such a line scan camera having an objective lens that is capable of scanning a range of selectable fields of view.

Still another object of this invention is to provide such a line scan camera that substantially eliminates unpredictable edge effects.

The present invention is a color line scan video camera for use in an inspection system. In a preferred embodiment, the line scan camera of the present invention derives from the scanned articles color component video signals corresponding to three separate preselected color components, thereby providing a substantially full-color representation of the articles. The line scan camera includes a prismatic beam splitter that separates the light received from the scanned articles into three light ray components, which are directed through separate color-selective filters to form three preselected spectral bands of light. The light within each of the spectral bands is imaged upon a different charge-coupled device line scan sensor that is bonded to the prismatic beam splitter and generates the color component video signal corresponding to the spectral band.

The line scan camera includes a variable magnification (i.e., zoom) objective lens arrangement having low chromatic aberration to uniformly transmit to the prismatic beam splitter substantially all visible light, including the light in each of the three spectral bands. The variable magnification of the objective lens allows it to form at the line scan sensors an image that is matched to the size of the photodetector array, regardless of the size of the object being imaged (i.e., the overall width of the articles on the conveyor belt). Conversely, the variable magnification of the objective lens allows it to deliver to the line scan sensors variable fields of view.

Although prior art monochrome line scan cameras have been employed in inspection systems, color line scan cameras have not been available because the alignment tolerances of the line scan sensors in such cameras have been unattainable. In particular, each photodetector in a 1024:1 array has dimensions of about 14 μm × 14 μm. As a consequence, each photodetector array has a width of 14 μm in a direction perpendicular to the row of 1024 photodetectors and must be aligned at least within about 3 μm. The optical components of conventional monochrome line scan cameras and conventional two-dimensional color video cameras render such a tolerance difficult to achieve.

In the present invention, however, a combination of selected optical components satisfies these alignment requirements to provide a color line scan video camera. In the preferred embodiment, the prismatic beam splitter includes three separate prism elements that are bonded together to form a rugged, unitary optical instrument capable of maintaining its alignment with a high degree of accuracy. The prismatic beam splitter is capable, therefore, of providing consistent spatial separation of the three spectral bands of light well within the 3 μm tolerance.

Moreover, the low chromatic aberration of the objective lens allows the prismatic beam splitter to adequately align each of the preselected spectral bands of light with all 1024 photodetectors in the corresponding photodetector array. By bonding the photodetector arrays to the prismatic beam splitter, the 3 μm tolerance is maintained for all of the photodetectors in the arrays. Each spectral band is, therefore, aligned with its corresponding photodetector array in a uniform manner to substantially eliminate the unpredictable edge effects characteristic of some color line scan cameras. As a result, high-speed inspection systems such as those used in the food product industry may utilize the full-color inspection capability and the 1000 Hz frame rates of high-resolution line scan sensors.

Additional objects and advantages of the present invention will be apparent from the detailed description of a preferred embodiment thereof, which proceeds with reference to the accompanying drawings.

BRIEF DESCRIPTION OF THE DRAWINGS

FIG. 8 is a fragmentary side view of a line scan sensor being aligned with a prismatic beam splitter.

DETAILED DESCRIPTION OF PREFERRED EMBODIMENT

Figure 2:
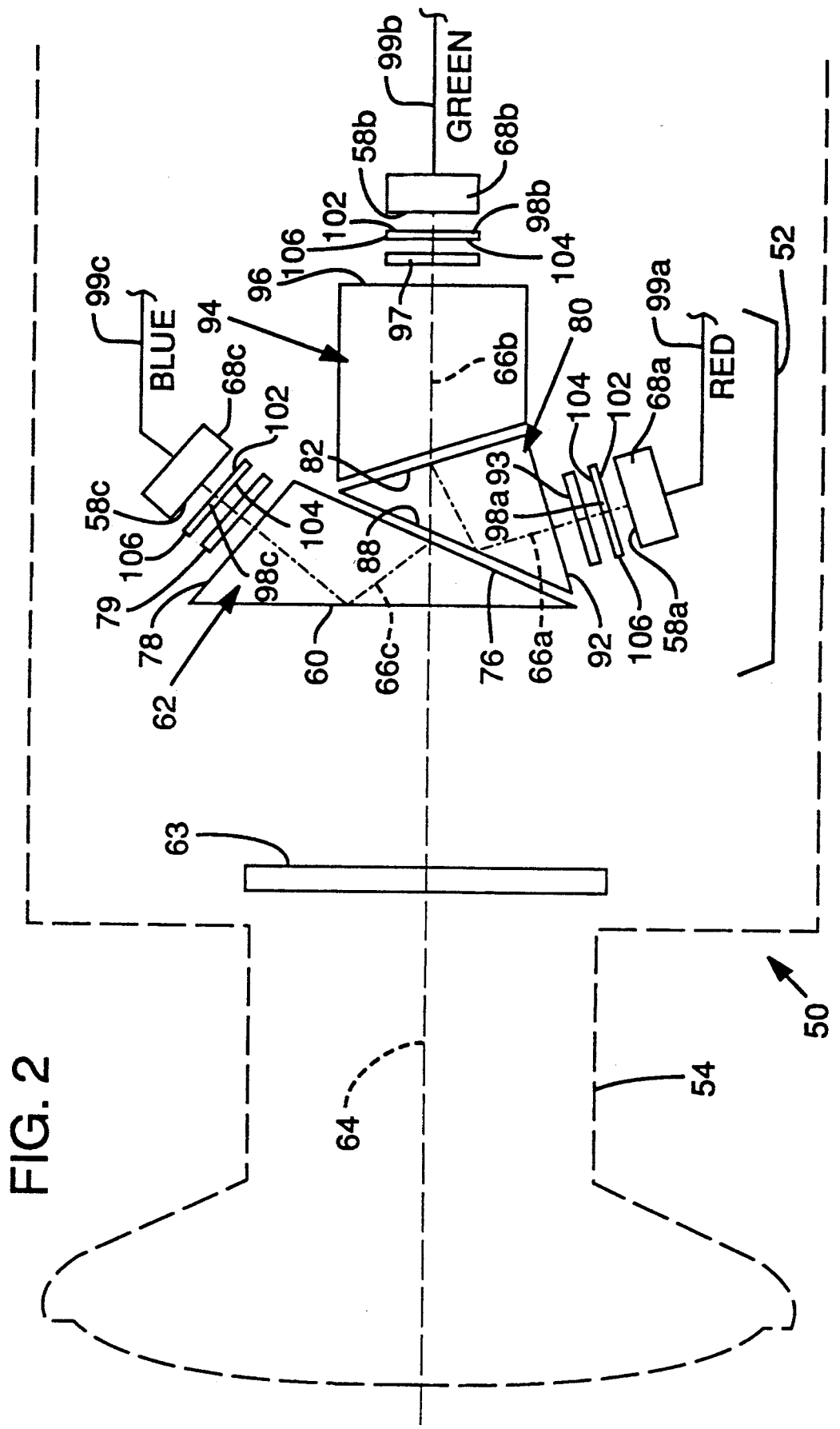
FIG. 2 is an exploded simplified side elevation view of the optical components included in the color line scan video of the present invention.

FIG. 2 is an exploded side elevation view of optical components in a color line scan video camera 50 of the present invention, which is compatible for use in inspection system 10. Color line scan camera 50 includes a prismatic beam splitter arrangement 52 that receives a wide spectrum of visible light from a variable magnification objective or zoom lens arrangement 54. In a preferred embodiment, color line scan camera 50 would be used in inspection system 10 at a position similar to that of prior art line scan video camera 12. The operation of color line scan camera 50 will be described herein, therefore, as a component of inspection system 10.

Figure 1:
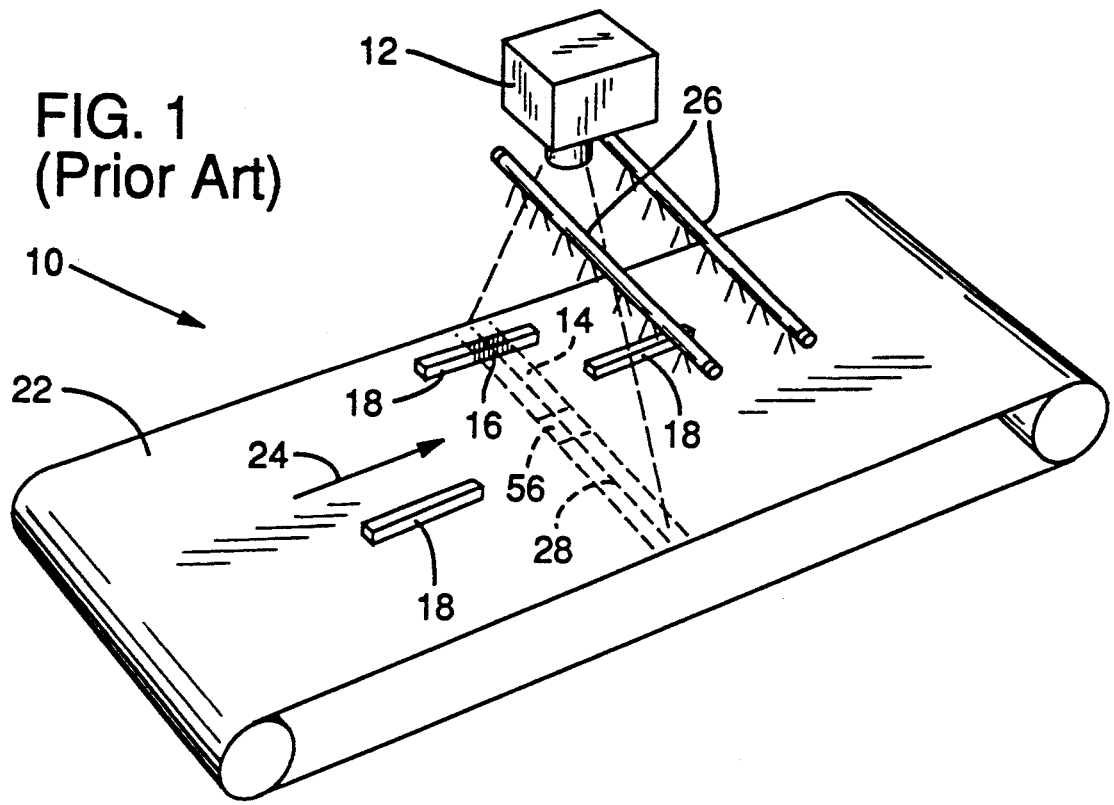
FIG. 1 is a schematic isometric view of a prior art line scan camera employed in an inspection system.

Zoom lens 54 delivers to prismatic beam splitter 52 source light reflected from a line scan area of a size corresponding to the magnification provided by zoom lens arrangement 54, which provides magnification factors of between one and fifteen. The magnification factor one provides to prismatic beam splitter 52 an image of line scan area 14 (FIG. 1), which extends completely across conveyor belt 22. The magnification factor fifteen provides to prismatic beam splitter 52 an image of a line scan area 56 (FIG. 1) that extends across about one-fifteenth of conveyor belt 16. A benefit of the smaller line scan areas provided by zoom lens magnification factors greater than one is that the resolution of camera 50 in those scanning areas is increased by the same factor.

Each of the line scan areas 14 and 56 has an aspect ratio of 1024:1 between its length along scanning axis 28 and its width perpendicular to scanning axis 28. The aspect ratios of line scan areas 14 and 56 are established by the arrangement or geometry of photodetector arrays 58a, 58b, and 58c that generate the color video signals, as will be described below in greater detail.

In operation, zoom lens 54 receives source light reflected from articles 18 being inspected and directs the reflected light toward prismatic beam splitter 52. The source light generated by light source 26 includes substantially uniform amounts of each wavelength of visible light, thereby corresponding to a nominally white light source. Zoom lens 54 is "color corrected" to provide low chromatic aberration (i.e., substantially uniform chromatic transmission characteristics). In the preferred embodiment, zoom lens 54 is a TV zoom lens Model J15x9.5B IRS, manufactured by Canon, Inc. of Japan.

Figure 3:
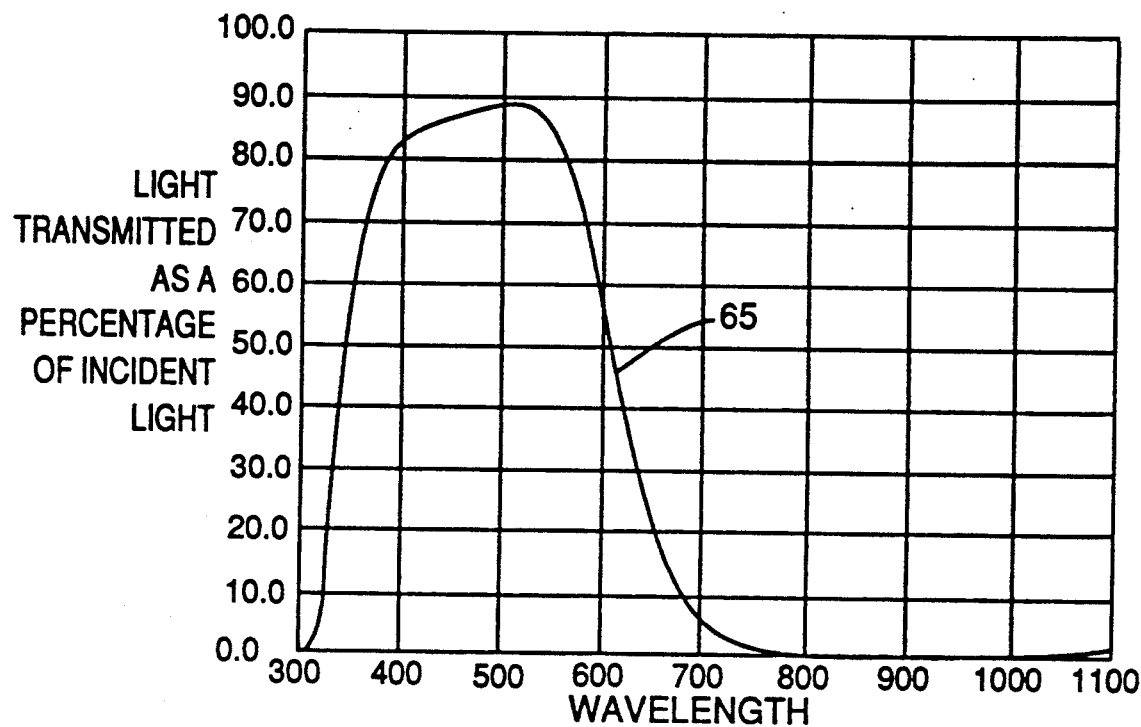
FIG. 3 is a graph showing the spectral transmission characteristics of an infrared cut filter employed in the color line scan camera of FIG. 2.

Prismatic beam splitter 52 receives at a receiving surface 60 of a receiving prism 62 a multiple visible wavelength input light ray transmitted through zoom lens 54 and an infrared cut filter 63 positioned along an optic axis 64. Infrared cut filter 63 (shown separated from receiving surface 60 for purposes of clarity) is a dielectric coating positioned to receive light transmitted through zoom lens 54 and to prevent infrared components of the light from being delivered to the beam splitter arrangement 52. FIG. 3 is a graph of the light transmission characteristics 65 of infrared cut filter 63 showing that light of wavelengths greater than about 750 nanometers is blocked, thereby allowing photodetector arrays 58a–58c to generate video signals that are not saturated by infrared light components.

Prismatic beam splitter 52, which is preferably color neutral, spatially separates the input light ray into first, second, and third light ray components that propagate along the light component optical paths 66c, 66a, and 66b, respectively. The light ray components include nominally uniform portions (i.e., about ⅓ each) of the input light ray.

Receiving prism 62 includes a first partially "silvered," color-neutral interface surface 76 that is oriented to separate the first light ray component from the second and third light ray components. The first light ray component is then internally reflected from receiving surface 60 and directed toward photodetector array 58c of a charge-coupled device line scan sensor 68c positioned adjacent a first exit surface 78. A multilayer dielectric optical bandpass filter 79 is applied to exit surface 78 by means of evaporation. (Bandpass filter 79 is shown separated from exit surface 78 for purposes of clarity.) Bandpass filter 79 transmits a predominantly blue spectral band of the first light ray component.

The orientation of interface surface 76 allows the second and third light ray components to propagate through to an intermediate prism 80. Intermediate prism 80 includes a partially "silvered," color-neutral second interface surface 82 that is oriented to separate the second light ray component from the third light ray component.

The second light ray component is then internally reflected from a receiving surface 88 of prism 80 and directed toward photodetector array 58a of a charge-coupled device line scan sensor 68a positioned adjacent a second exit surface 92. A multi-layer dielectric optical bandpass filter 93 is applied to exit surface 92 by means of evaporation. (Bandpass filter 93 is shown separated from exit surface 92 for purposes of clarity.) Bandpass filter 93 transmits a predominately red spectral band of the second light ray component. Receiving surface 88 is disposed substantially parallel to first interface surface 76 of receiving prism 62.

The orientation of second interface surface 82 allows the third light ray component to propagate through to an exit prism 94 having a third exit surface 96 adjacent to which photodetector array 58b of a charge-coupled device line scan sensor 68b is positioned. A multi-layer dielectric optical bandpass filter 97 is applied to exit surface 96 by means of evaporation. (Bandpass filter 97 is shown separated from exit surface 96 for purposes of clarity.) Bandpass filter 97 transmits a predominately green spectral band of the first light ray component.

In the preferred embodiment, prismatic beam splitter 52 is a Model SSB-B1426 manufactured by Canon, Inc. of Japan. The commercially available beam splitter is modified in two respects. In a first modification, a filter wheel (not shown) adapted to optimize imaging sensitivity in different outdoor lighting conditions is removed. The filter wheel is unnecessary under the uniform lighting conditions provided by light source 26 in inspection system 10. In a second modification, infrared cut filter 63 is applied to receiving surface 60 of prism 62.

As an alternative to the use of bandpass filters 79, 93, and 97 on the exit surfaces of beam splitter 52, dichroic or "cold" mirrors could be applied to interface surfaces 76 and 82 in a manner known in the art. As a result, photodetector arrays 58a, 58b, and 58c receive the respective red, green, and blue spectral components of the entire input light ray. In contrast, bandpass filters 79, 93, and 97 deliver to respective photodetector arrays 58c, 58a, and 58b spectral components of only the light ray components. These spectral components have nominally one-third the intensities of the spectral components delivered to the photodetectors by the alternative beam splitter having dichroic or "cold" mirrors. It will be appreciated, therefore, that the alternative beam splitter would be preferred in lower-light conditions or to perform very high-speed inspection.

Line scan sensors 68a, 68b, and 68c generate color component video signals corresponding to the intensities of light in the red, green, and blue spectral bands, respectively. The color component video signals are processed, as described below in greater detail, to identify preselected physical characteristics of the articles 14. In a preferred embodiment, line scan sensors 68a, 68b, and 68c are Model 7804A charge-coupled device line scan sensors manufactured by Thompson CSF of France. Photodetector arrays 58a, 58b, and 58c of such line scan sensors comprise photodiodes that generate the color component video signals and transfer the signals in parallel to integrated charge-coupled device shift registers (not shown). The video signals are then shifted in a serial manner from the shift registers of line scan sensors 68a, 68b, and 68c to respective video outputs 99a, 99b, and 99c.

Figure 4:
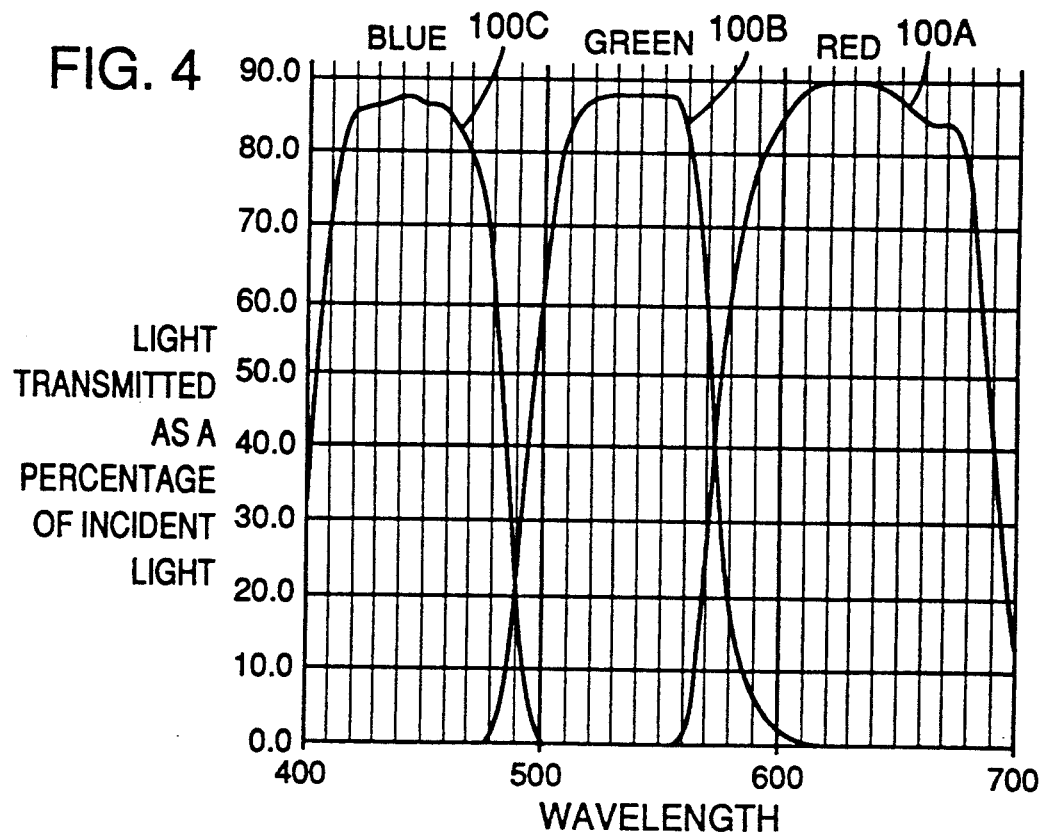
FIG. 4 is a graph showing the spectral transmission characteristics of the prismatic beam splitter shown in FIG. 2.

FIG. 4 is a graph showing the spectral components 100a, 100b, and 100c of the red, green, and blue spectral bands formed by bandpass filters 93, 97, and 79, respectively. Each of the spectral components 100a, 100b, and 100c is shown as a percentage of substantially white light in a corresponding light ray component. The red, green, and blue spectral bands above the 40% transmission level correspond to the respective nominal wavelength ranges of 575 nm to 690 nm, 495 nm to 570 nm, and 400 nm to 485 nm.

Secured between line scan sensors 68a, 68b, and 68c and exit surfaces 92, 96, and 78 are respective ultraviolet light-transmitting spacers 98a, 98b, and 98c that facilitate the proper positioning of the line scan sensors. Each of spacers 98a, 98b, and 98c includes substantially parallel, flat, opposed sides 102 and 104, has a thickness of between about 3.96 mm and 4.12 mm and is formed of sapphire or another ultraviolet light-transmitting material such as quartz or BK-7 glass. The method of attaching spacers 98 is described below with particular reference to line scan sensor 68b and exit surface 96, but is similarly applicable to line scan sensors 68a and 68c and exit surfaces 92 and 78, respectively.

Line scan sensor 68b, exit surface 96, and spacer 98b are bonded together by an ultraviolet light-sensitive adhesive that cures when exposed to ultraviolet light. The ultraviolet light-sensitive adhesive is applied to surface 102 of spacer 98b, and the light receiving window of line scan sensor 68b is placed against surface 102 in contact with the adhesive. Ultraviolet light is transmitted through spacer 98b to cure the adhesive, thereby securing spacer 98b against line scan sensor 68b to form a bonded article 120 (FIG. 5). Side 104 of spacer 98b is then placed against bandpass filter 97 on exit surface 96 with ultraviolet light-sensitive adhesive therebetween.

Since the adhesive will not cure until exposed to ultraviolet light, the orientation and position of line scan sensor 68b and spacer 98b may be precisely adjusted until photodetector array 58b is properly aligned to receive line scan information. Once such an alignment has been achieved, ultraviolet light is transmitted through side margins 106 of spacer 98b to cure the adhesive positioned between side 104 and exit surface 96. It will be appreciated, therefore, that the view of line scan sensor 68b and spacer 98b in FIG. 2 is exploded along optic path 66b.

The delay in the curing of the adhesive until it is exposed to ultraviolet light provides sufficient time to align photodetector array 58b. Since ultraviolet light-transmitting optical components are relatively expensive, zoom lens 54 and prismatic beam splitter 52 preferably do not include such components and transmit virtually no ultraviolet light. As a result, the ultraviolet light-transmitting properties of spacer 98 are necessary to allow the ultraviolet light to reach the adhesive and cure it.

Figure 5A:
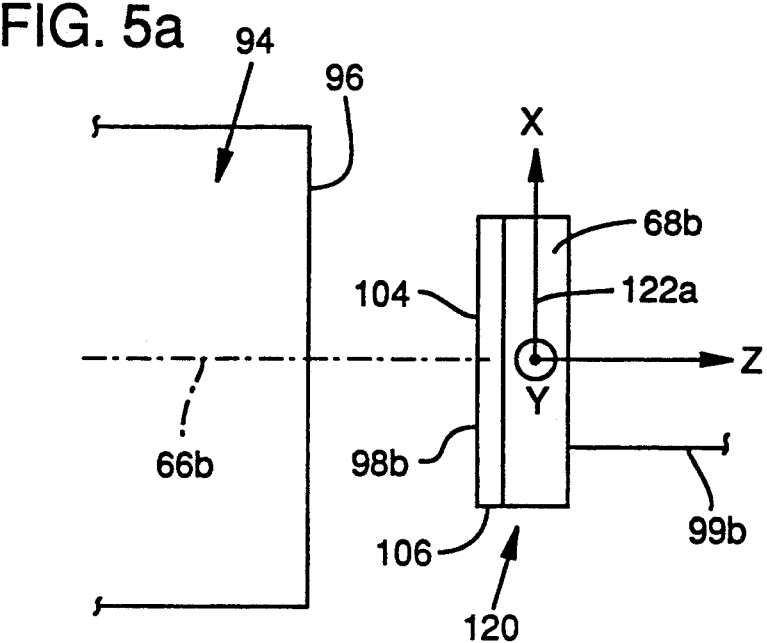
FIG. 5a is a fragmentary side elevation view of optical components being assembled for the color line scan video camera of FIG. 2.
Figure 5B:
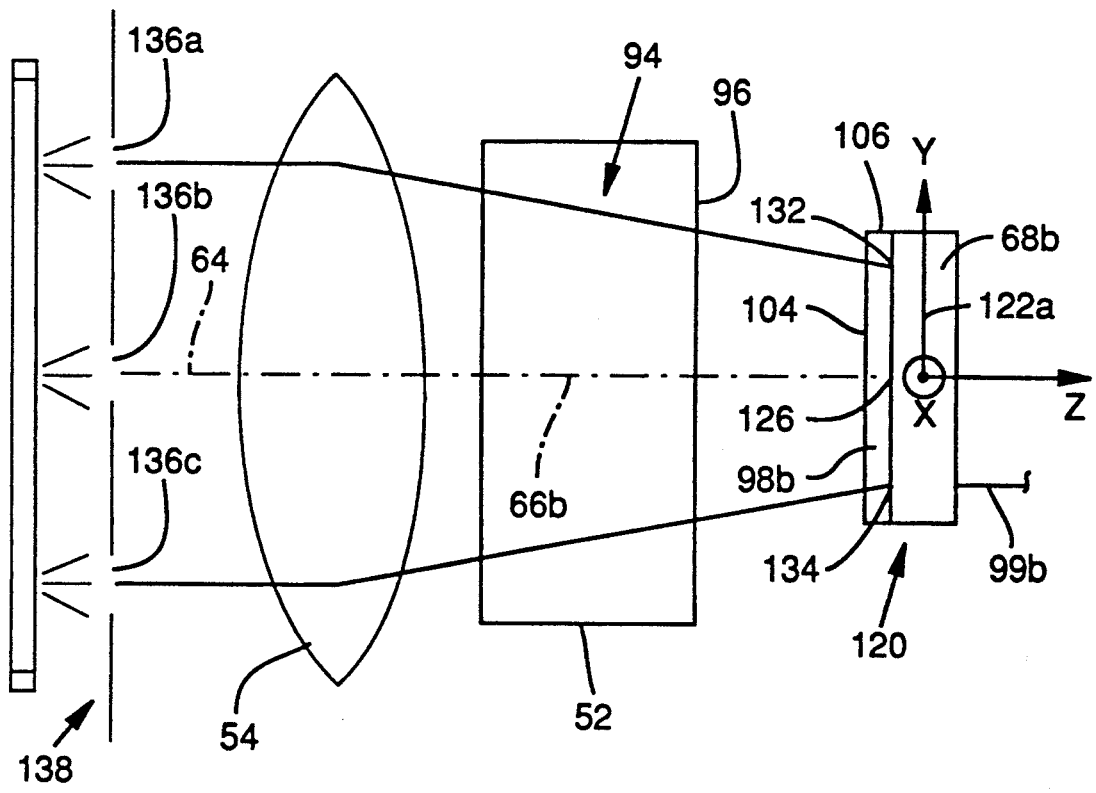
FIG. 5b is a schematic plan view of the optical components being assembled for the color line scan video camera.
Figure 6:
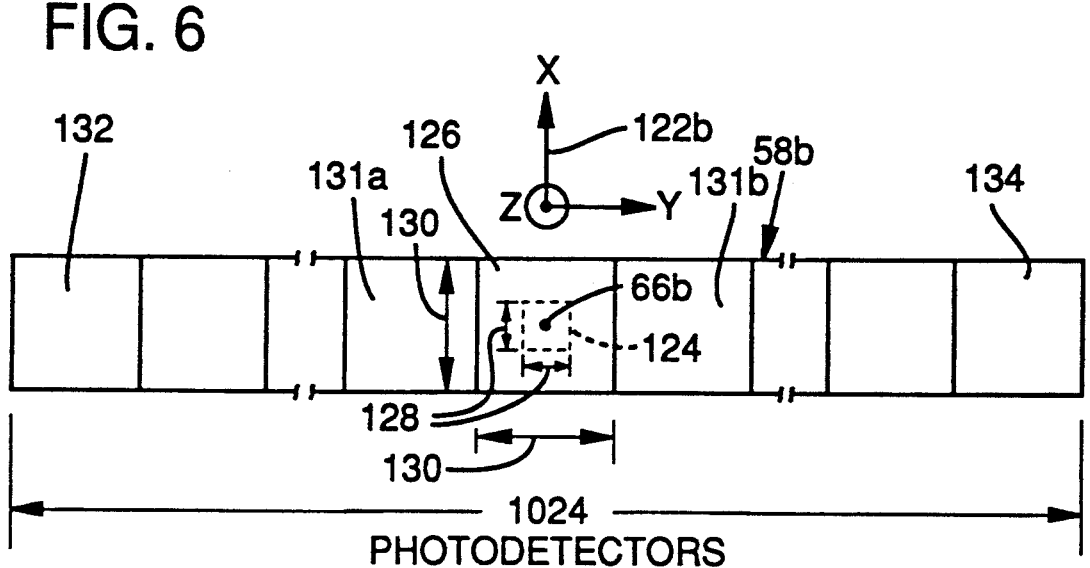
FIG. 6 is a front fragmentary view of a photodetector array employed in the color line scan video camera of FIG. 2.

With reference to FIGS. 5a, 5b, and 6, the alignment of bonded article 120 with exit surface 96 of prism 94 is achieved by securing prismatic beam splitter 52 in a stationary clamp (not shown) and employing a 6 degree of motion micrometer-controlled manipulation stage (not shown) to engage surface 104 of bonded article 120 with exit surface 96. The manipulation stage provides bonded article 120 with lateral motion along and rotational motion about Cartesian x-, y-, and z-axes defined by a coordinate origin 122a (FIG. 5). Coordinate origin 122b (FIG. 6) is offset from its actual location for purposes of clarity to show the relative directions of the x-, y-, and z-axes. Coordinate origin 122b does not show, therefore, the axes about which rotational motion occurs.

An operator employs the manipulator stage to adjust rotational motion about the x- and y-axes to orient surface 104 substantially parallel to exit surface 96. Bonded article 120 is then moved along the z-axis so that surface 104 engages the ultraviolet light-sensitive adhesive on exit surface 96. As described in greater detail below, the thickness of spacer 98b is selected to assure that photodetector array 58b is precisely positioned at the image or back focal surface of zoom lens 54.

The operator employs the manipulator stage to provide lateral motion along the x- and y-axes to position a designated alignment area 124 of a center-most photodetector 126 in alignment with light ray component optical path 66b. Alignment area 124 is located at about the center of photodetector 126 and has dimensions 128 that are slightly less than the size of the dimensions 130 of photodetector 126. Since each of the photodetectors in array 58b has dimensions of about 14 μm × 14 μm.

Three spaced-apart point sources of light 136a, 136b, and 136c, which are arranged in a line and designated alignment target 138, are imaged on photodetector array 58b by zoom lens 54 and beam splitter 52. Simultaneously, an oscilloscope test probe is connected to output 99b to allow an oscilloscope to receive and measure the magnitude of the video signal generated by line scan sensor 68b. The video signal includes spurious video signal components that appear to be generated by the photodetectors next adjacent to the photodetectors onto which the point sources of the alignment target are imaged. The spurious video signals are generated as a consequence of the non-ideal operation of the charge-coupled device shift register in line scan sensor 68b.

Bonded article 120 is first positioned and oriented such that middle point source 136b of alignment target 138 is aligned with and focused upon center-most photodetector 126. This alignment is achieved by positioning bonded article 120 so that the video signal component representing middle point source 136b coincides with the center-most portion of the video signal representation rendered by the oscilloscope. The position and orientation of bonded article 120 are then adjusted so that the magnitude of the video signal generated by center-most photodetector 126 is maximized and the magnitudes of the spurious video signals appearing to be generated by next adjacent photodetectors 131a and 131b (FIG. 6) are of equal magnitude. Equalizing the magnitudes of the spurious video signals precisely centers bonded article 120 along the y-axis.

Figure 7:
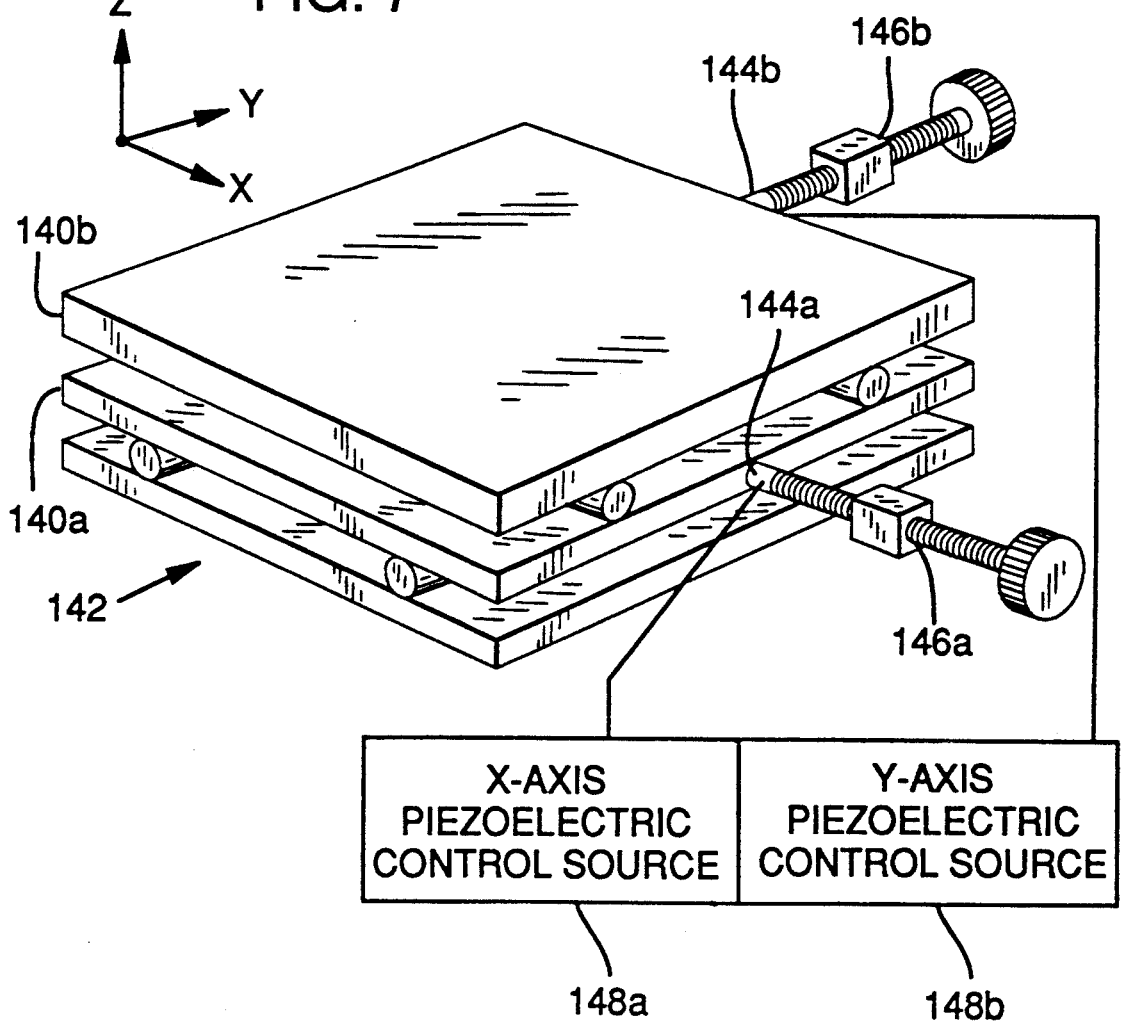
FIG. 7 is a simplified isometric view of the x- and y-axis translation tables in a preferred manipulation stage used in the assembly of the color line scan video camera of FIG. 2.

FIG. 7 shows schematically an x-axis translation table 140a and a y-axis translation table 140b of a preferred manipulation stage 142. Manipulation stage 142 includes piezoelectric transducers 144a and 144b secured between x- and y-axis micrometer controls 146a and 146b and translation tables 140a and 140b, respectively. It will be appreciated that manipulation stage 142 includes for translation along the z-axis and rotation about the x-, y-, and z-axes. These other tables are not shown in FIG. 7 for purposes of simplicity.

The micrometer controls of a conventional manipulator stage are incapable of providing repeatable motion of adequate resolution to achieve the proper alignment along the x- and y-axes. Manipulation stage 142 includes piezoelectric transducers 140a and 140b to provide the sufficiently high resolution control of the positioning. In operation, micrometer controls 146a and 146b provide relatively coarse positioning of bonded article 120 along the x- and y-axes, while piezoelectric transducers 144a and 144b provide the fine positioning. In particular, piezoelectric transducers 144a and 144b move translation tables 140a and 140b by amounts corresponding to the amplitudes of piezoelectric control signals generated by control signal source 148a and 148b, respectively. In a preferred embodiment, piezoelectric transducers 144a and 144b are Model P-820.1 transducers manufactured by Polytech Optronics of Costa Mesa, Calif.

After engaging the ultraviolet light-sensitive adhesive, bonded article 120 is rotated about the z-axis to align outer-most photodetectors 132 and 134 with respective peripheral point-sources 136a and 136c of alignment target 138. To provide fine positioning in the rotation about the z-axis, a piezoelectric transducer is employed in the manner described above with reference to line motion along the x- and y-axes. Once such alignment of outer-most photodetectors 132 and 134 has been achieved, ultraviolet light is directed through side margins 106 of spacer 98b to cure the ultraviolet light-sensitive adhesive.

The thickness of spacer 98b must be precisely selected so that photodetector array 58b is positioned at the image or back focal surface of zoom lens 54. To determine the proper thickness of spacer 98b, a focal surface measurement process employs a preselected or test bonded article having a precisely measured distance from its photodetector array to the outer surface of its spacer. The spacer of the test bonded article is relatively thin. The measurement process entails identifying the position of the zoom lens back focal surface with the test bonded article and then selecting an appropriate spacer 98b and line scan sensor 68b to position photodetectors 58b within a tolerance of about ±0.01 mm from the focal surface.

More specifically, brass shims (not shown) are positioned between zoom lens 54 and beam splitter 52 so that the focal surface is located about 3.0 mm beyond exit surface 96. The test bonded article is aligned with the alignment target in the manner described above. The test bonded article is then moved by the manipulator stage along the z-axis while the alignment target is focused on the photodetector array of the test bonded article. The position of the focal surface is identified when the magnitude of the video signal generated by the centermost photodetector is maximized.

The distances between exit surfaces 78, 92, and 96 and the corresponding focal surfaces typically differ by less than about 0.30 mm. For example, exit surfaces 78, 92, and 96 could be positioned 3.00 mm, 2.85 mm, and 3.10 mm, respectively, from the corresponding focal surfaces. Spacers 98a, 98b, and 98c and line scan sensors 68a, 68b, and 68c are matched to position respective photodetector arrays 58a, 58b, 58c at a uniform separation (e.g., 0.4 mm±0.02 mm) from their corresponding focal surfaces. The uniform separation between photodetector arrays 58a, 58b, and 58c and their corresponding focal surfaces is then eliminated to within the ±0.01 mm tolerance by changing the brass shims that separate zoom lens 54 and beam splitter 52.

With reference to FIG. 8, a front surface 150 of a photodetector window 152 is a particular distance 154 from photodetector array 58b. Distance 154 ranges between 1.13 mm and 1.24 mm and is, therefore, measured for each line scan sensor. Similarly, each spacer 98 has a measured thickness 156 of between 0.156 inch and 0.162 inch. Line scan sensor 68b and spacer 98b are selected, therefore, so that photodetector array 58b, can be positioned at the uniform separation from its focal surface. An air gap of about 0.5 milli-inch remains between exit surface 96 and front surface 104 of spacer 98b to accomodate the adhesive material.

Maintenance of the high resolution alignment between bonded articles 120 and beam splitter 52 is facilitated by reducing the forces pulling against the different components of the system. With reference to FIG. 8, line scan sensor 68b is coupled to surface mount components 158b with a socket 160b to reduce their weight and, thereby, the force exerted against the adhesive bond to beam splitter 52. Similarly, output 98b includes a flexible silicone-coated, fine-wire shielded, coaxial cable of the type manufactured by Wiretek Wire as Model No. AS450-3250SR. A tin-plated sheet steel box 162b contains surface mount components 158b to shield them from electromagnetic fields. A steel plate 164b mounted on the interior of shielding box 162b is engaged by a magnet 166 to secure the line scan sensor 68b to manipulation stage 142 without introducing into bonded article 120 the deformation that can be caused by a conventional friction and pressure-based clamp.

In operation, prisms 62, 80, and 94 of prismatic beam splitter 52 are bonded together to form a rugged, unitary optical instrument capable of maintaining its alignment with a high degree of accuracy. Prismatic beam splitter 52 is capable, therefore, of providing consistent spatial separation of the red, green, and blue spectral bands of light well within a tolerance of 3 $\mu$m. Moreover, the low chromatic aberration characteristics of zoom lens 54 introduces a maximum image misalignment at outer-most photodetectors 132 and 134 of less than about 3 $\mu$m. As a result, secure alignment of prismatic beam splitter 52 cooperates with the low chromatic aberration characteristics of zoom lens 54 to provide the color imaging capability of color line scan video camera 50.

Figure 9:
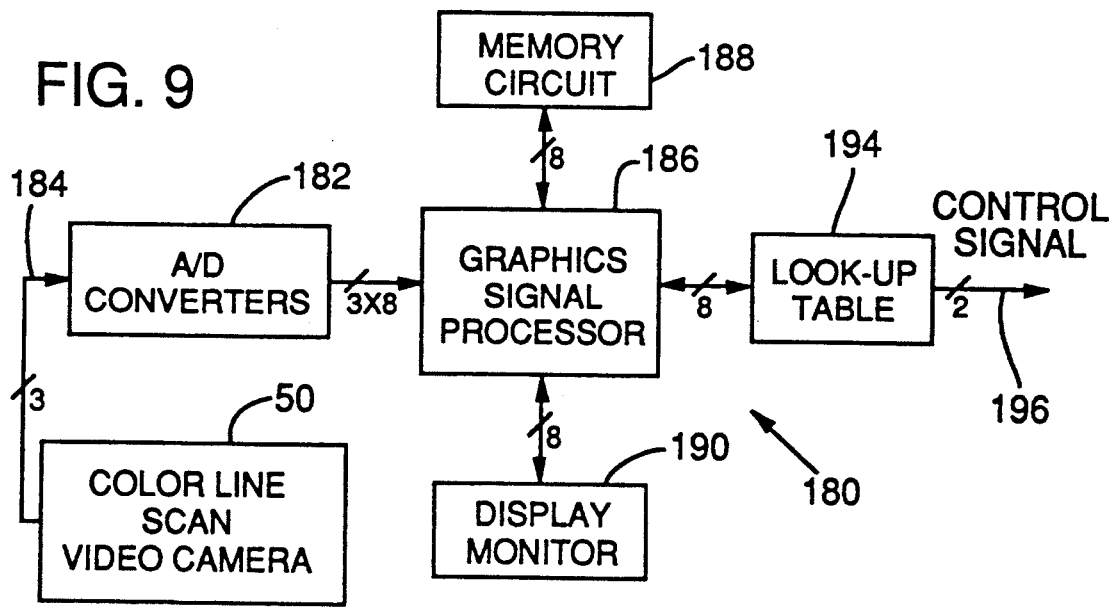
FIG. 9 is a simplified block diagram of the data processing circuitry associated with the color line scan camera of FIG. 2.

FIG. 9 is a simplified block diagram of the data processing apparatus 180 for processing the color component video signals generated by line scan sensors 68a, 68b, and 68c of color line scan camera 50. Data processing apparatus 180 includes an analog-to-digital converter 182 that receives at an input 184 the color component video signals generated by line scan sensors 68a, 68b, and 68c. It will be appreciated that analog-to-digital converter 182 could alternatively include a separate converter circuit for each of the line scan sensors or could include a multiplexer that delivers the color component video signals successively to a single converter circuit.

Analog-to-digital converter 182 delivers digitized color component video signals to a graphics signal processor 186 that stores the signals in a memory circuit 188 and selectively delivers corresponding video control signals to a display monitor 190. A digital look-up table 194 configured as a random access memory circuit or a programmable logic array stores information concerning particular characteristics (e.g., defect/non-defect) of scanned articles 18 in accordance with preselected magnitudes of the color component video signals.

For example, data locations within look-up table 194 are identified by the magnitude of the color component video signal corresponding to each of the red, green, and blue spectral bands, as described in U.S. Pat. No. 5,085,325, of Jones et al. for COLOR SORTING SYSTEM AND METHOD, issued Feb. 4, 1992 and assigned to the assignee of the present application. In connection with, for example, defect detection in a food processing apparatus, each of the information locations in the look-up table may correspond either to a defect or non-defect characteristic in the food product. As a result, each possible color identified by line scan camera 50 corresponds to a defective or a non-defective portion of the articles being processed. The defect characteristics corresponding to a particular color are delivered to an output 196 of look-up table 194 and are employed by the inspection system as a control signal for controlling subsequent processing or sorting of the article.

It will be obvious to those having skill in the art that many changes may be made to the details of the above-described preferred embodiment of the present invention without departing from the underlying principles thereof. For example, the color line scan video camera could be employed in inspection stations for sorting nonfood articles such as recyclable bottles or for inspecting successive individual articles one at a time. The scope of the present invention should be determined, therefore, only by the following claims.

We claim:

1. A method for positioning and aligning a first photodetector array relative to a first exit surface of a prismatic beam splitter of a color inspection camera, comprising the steps of:

directing light from an alignment target through the prismatic beam splitter to the first exit surface;

positioning with a micrometric manipulator the first photodetector array adjacent to the first exit surface of the prismatic beam splitter;

aligning the first photodetector array with an electromechanical manipulator coupled to the micrometric manipulator such that the alignment target is received by predetermined photodetectors in the first photodetector array, the electromechanical manipulator providing a finer degree of manipulation than the micrometric manipulator; and bonding the first photodetector array to the first exit surface of the prismatic beam splitter.

2. The method of claim 1 in which the micrometric manipulator includes a micrometer-based manipulator stage capable of translating, rotating and spacing the first photodetector array relative to the first exit surface of the prismatic beam splitter.

3. The method of claim 1 in which the electromechanical manipulator includes a piezoelectric transducer coupled to the micrometric manipulator.

4. The method of claim 1 in which the alignment target includes three spaced-apart point sources of light arranged in a line.

5. The method of claim 1 in which the first photodetector array is a linear array having at least 1000 photodetectors each having a cross-sectional dimension of about 14 micrometers.

6. The method of claim 5 in which the alignment light target is imaged on predetermined ones of the photodetectors of the first photodetector array to an accuracy of within about three micrometers of the center of the cross-sectional dimension.

7. The method of claim 1 further including the steps of:

positioning with the micrometric manipulator a second photodetector array adjacent to a second exit surface of the prismatic beam splitter;

aligning the second photodetector array with the electromechanical manipulator coupled to the coarse manipulator such that the alignment light target is imaged on corresponding predetermined photodetectors in the first and second photodetector arrays; and bonding the second photodetector array to the second exit surface of the prismatic beam splitter.

* * * * *